United States Patent
Litman et al.

(10) Patent No.: US 11,998,289 B2
(45) Date of Patent: Jun. 4, 2024

(54) METHOD AND SYSTEM FOR AUTONOMOUS THERAPY

(71) Applicant: Aescape, Inc., New York, NY (US)

(72) Inventors: Eric A. Litman, Brooklyn, NY (US); David N. Walsh, Brooklyn, NY (US); Charles Paul Pace, Brooklyn, NY (US); Matthew DiCicco, Brooklyn, NY (US)

(73) Assignee: Aescape, Inc., New York, NY (US)

( * ) Notice: Subject to any disclaimer, the term of this patent is extended or adjusted under 35 U.S.C. 154(b) by 388 days.

(21) Appl. No.: 17/319,065

(22) Filed: May 12, 2021

(65) Prior Publication Data

US 2022/0387118 A1 Dec. 8, 2022

Related U.S. Application Data

(60) Provisional application No. 63/023,839, filed on May 12, 2020, provisional application No. 63/023,844, (Continued)

(51) Int. Cl.
 *A61B 34/30* (2016.01)
 *A61B 34/10* (2016.01)
(52) U.S. Cl.
 CPC .............. *A61B 34/30* (2016.02); *A61B 34/10* (2016.02); *A61B 2034/101* (2016.02)
(58) Field of Classification Search
 CPC .... A61B 34/30; A61B 34/10; A61B 2034/101
 See application file for complete search history.

(56) References Cited

U.S. PATENT DOCUMENTS 5,876,325 A 3/1999 Mizuno
6,494,851 B1 12/2002 Becher
(Continued)

FOREIGN PATENT DOCUMENTS

CN 203017580 U 6/2013
CN 204684116 U 10/2015
(Continued)

OTHER PUBLICATIONS

Hu et al., "A massage robot based on Chinese massage therapy", 2013, Emerald Group Publishing, The Industrial Robot: An International Journal, vol. 40, No. 2, pp. 158-172. (Year: 2013).
(Continued)

*Primary Examiner* — Jaime Figueroa
*Assistant Examiner* — Mohamad O El Sayah
(74) *Attorney, Agent, or Firm* — Van Pelt, Yi & James LLP

(57) ABSTRACT

A system, method, and apparatus are provided for a robotic system effecting autonomous therapy or treatment of a body having soft and/or hard tissue. A system, method, and apparatus are provided for a robotic control system having a fused sensing stream for predicting the deformation of a robotic end effector and the tissue that the end effector is in contact with using, e.g., a Finite Element Analysis (FEA) model. The model updates provide adjustment parameters for the control system to compensate for changes in the mechanical nature of the robotic end effector and the characteristics and/or movement of the tissue being treated by the robotic end effector.

26 Claims, 12 Drawing Sheets

Related U.S. Application Data filed on May 12, 2020, provisional application No. 63/023,833, filed on May 12, 2020.

(56) References Cited

U.S. PATENT DOCUMENTS

| | | |
|---|---|---|
| 6,585,668 B2 | 7/2003 | Nissim |
| 6,607,499 B1 | 8/2003 | Becher |
| D517,218 S | 3/2006 | Kalen |
| D637,304 S | 5/2011 | Feuerabend et al. |
| D637,305 S | 5/2011 | Feuerabend et al. |
| D644,675 S | 9/2011 | Abed |
| D665,093 S | 8/2012 | Sedic |
| 10,034,813 B1* | 7/2018 | Silver .................. A61B 34/30 |
| 10,034,814 B2 | 7/2018 | Zhang |
| D831,769 S | 10/2018 | Tranchard |
| D833,028 S | 11/2018 | Olivares et al. |
| 10,390,755 B2 | 8/2019 | Goodall |
| D861,829 S | 10/2019 | Wang |
| D867,609 S | 11/2019 | Couto et al. |
| 11,197,799 B2 | 12/2021 | Tian |
| 11,338,443 B2 | 5/2022 | Eyssautier |
| 11,475,630 B2 | 10/2022 | Tian |
| 11,529,900 B2 | 12/2022 | Kim |
| 11,654,551 B2 | 5/2023 | Huang |
| 2001/0014781 A1 | 8/2001 | Nissim |
| 2002/0013641 A1 | 1/2002 | Nourbakhsh et al. |
| 2007/0000374 A1 | 1/2007 | Clark et al. |
| 2007/0192910 A1 | 8/2007 | Vu et al. |
| 2010/0261530 A1 | 10/2010 | Thomas |
| 2011/0112549 A1* | 5/2011 | Neubach .................. A61B 34/20 606/130 |
| 2015/0351999 A1 | 12/2015 | Brouse |
| 2016/0242995 A1* | 8/2016 | Karkkainen ............ A61H 23/02 |
| 2017/0079871 A1 | 3/2017 | Zhang |
| 2017/0123487 A1* | 5/2017 | Hazra .................. G06F 3/04845 |
| 2017/0156662 A1 | 6/2017 | Goodall |
| 2017/0258598 A1* | 9/2017 | Radermacher ......... A61F 2/4657 |
| 2017/0266077 A1* | 9/2017 | Mackin ............... A61G 13/1235 |
| 2017/0281254 A1 | 10/2017 | Bonutti |
| 2019/0000447 A1* | 1/2019 | Shelton, IV .......... A61B 17/068 |
| 2019/0160684 A1* | 5/2019 | Gu ........................ B25J 13/087 |
| 2019/0167512 A1* | 6/2019 | Forsythe .................. A61H 7/00 |
| 2019/0381271 A1 | 12/2019 | Jo |
| 2020/0055195 A1 | 2/2020 | Ignakov |
| 2020/0113636 A1* | 4/2020 | Chino .................... A61B 90/37 |
| 2020/0121556 A1 | 4/2020 | Tian et al. |
| 2020/0126297 A1* | 4/2020 | Tian .......................... G06T 7/75 |
| 2020/0206913 A1* | 7/2020 | Kaehler ................. B25J 9/1612 |
| 2020/0281805 A1* | 9/2020 | Qiu .......................... A61H 1/00 |
| 2020/0391021 A1* | 12/2020 | Sachs ................ A61N 1/36132 |
| 2021/0085558 A1 | 3/2021 | Shin |
| 2021/0154852 A1* | 5/2021 | Eyssautier ............ G05B 19/401 |
| 2021/0155136 A1 | 5/2021 | Kim |
| 2022/0133589 A1* | 5/2022 | Gruneberg ............. A61H 37/00 601/1 |
| 2022/0134551 A1 | 5/2022 | Litman et al. |
| 2022/0387118 A1 | 12/2022 | Litman |
| 2022/0388165 A1 | 12/2022 | Walsh et al. |
| 2022/0388168 A1 | 12/2022 | Litman et al. |
| 2022/0414291 A1 | 12/2022 | Eyssautier |

FOREIGN PATENT DOCUMENTS

| | | |
|---|---|---|
| CN | 206416184 U | 8/2017 |
| CN | 111053530 A | 4/2020 |
| CN | 113908035 A | 1/2022 |
| SG | 10201809094 A1 | 5/2020 |
| WO | WO-2021116554 A1 | 6/2021 |
| WO | WO-2021231663 A3 | 2/2022 |
| WO | WO-2022056181 A1 | 3/2022 |

OTHER PUBLICATIONS

Luo et al., "Human Body Trajectory Generation Using Point Cloud Data for Robotics Massage Applications", 2014 IEEE International Conference on Robotics & Automation (ICRA), Hong Kong Convention and Exhibition Center May 31-Jun. 7, 2014. Hong Kong, China, pp. 5612-5617 (Year: 2014).

Meera et al., "Path planning and motion control for a 3 DOF massaging robot," 2016 International Conference on Robotics and Automation for Humanitarian Applications (RAHA), Amritapuri, India, 2016, pp. 1-6, doi: 10.1109/RAHA.2016.7931883. (Year: 2016).

Minyong et al., "Expert massage motion control by multi-fingered robot hand," Proceedings 2003 IEEE/RSJ International Conference on Intelligent Robots and Systems (IROS 2003) (Cat. No. 03CH37453), Las Vegas, NV, USA, 2003, pp. 3035-3040 vol.3, (Year: 2003).

Si et al., "Green Internet of Things Application of a Medical Massage Robot With System Interruption," IEEE Access, vol. 7, pp. 127066-127077, 2019, doi: 10.1109/ACCESS.2019.2939502. (Year: 2019).

David, Pradeep, "Cobots—A helping hand to the healthcare industry," Nov. 24, 2017, Universal Robots, 6 pages.

Screen captures from YouTube video clip entitled "Robots can now give full-body personalized massages at home," 11 pages, uploaded Jul. 21, 2020, New Scientist, Retrieved from Internet: https://www.youtube.com/watch?v=t59TXsK1a6c.

Ulanoff, Lance, "Massage Robotics wants you to come and be touched by a robot—if that's your thing," Jan. 6, 2022, Techradar, The source for Tech Buying Advice, 13 pages.

International Search Report and Written Opinion for Application No. PCT/US2021/032111, dated Jan. 24, 2022, 11 pages.

International Search Report and Written Opinion for Application No. PCT/US2021/049741, dated Feb. 7, 2022, 5 pages.

Kraus, Rachel, "Bow down before this $310,000 massage megarobot, human: Who knew the robot uprising would be so good on the shoulders?," Health & Wellness Artificial Intelligence, Dec. 30, 2021, https://mashable.com/article/massage-robot-.

Ex Parte Quayle Action for U.S. Appl. No. 29/732,265, mailed Dec. 2, 2022, 4 pages.

Massage instruments. (Desig - ©Questel) orbit.com. [Online PDF compilation of references selected by examiner] 17 pgs. Print Dates Range Feb. 24, 2004-Feb. 14, 2020 [Retrieved Nov. 18, 2022] https://www.orbit.com/export/LI CZAH96 B/pdf4/e9bd54bf-4351-4947- 8aae-2394fdea7fed-013045.pdf (Year: 2022).

* cited by examiner

METHOD AND SYSTEM FOR AUTONOMOUS THERAPY

CROSS-REFERENCE TO RELATED APPLICATION(S)

This application claims priority to U.S. Provisional Patent Application No. 63/023,833, entitled METHOD AND SYSTEM FOR AUTONOMOUS OBJECT MANIPULATION, filed on May 12, 2020; U.S. Provisional Patent Application No. 63/023,839, entitled METHOD AND SYSTEM FOR AUTONOMOUS BODY INTERACTION, filed on May 12, 2020; and, U.S. Provisional Patent Application No. 63/023,844, entitled METHOD AND SYSTEM FOR AUTONOMOUS THERAPY, filed on May 12, 2020, and incorporates each of the three aforementioned provisional patent applications in its entirety by reference hereto.

COPYRIGHT AND TRADEMARK NOTICE

Portions of the disclosure in this patent application contain material which is subject to copyright and/or trademark protection. The patent application owner has no objection to the facsimile reproduction of the published patent application or any resulting granted patent, as it appears in the U.S. Patent and Trademark Office records, but otherwise reserves all copyright and trademark rights whatsoever throughout the world.

FIELD OF INVENTION

The present invention relates to a system, method, and apparatus for autonomous therapy. More specifically, the present invention relates to a system, method, and apparatus for determining and/or executing the motion of a robot to assess and treat soft body tissue.

BACKGROUND OF INVENTION

Robotics have been used for various applications, including assembly manufacturing and device testing. Such robotics have been used to test or manufacture textiles and devices. Other robotics have been used in medical surgery, requiring slow, precise movement. Often, the robotics are controlled in real-time, such as those robotics used in medical procedures, in order to control and monitor the actions of the robotics.

Soft body objects, such as body tissue, may not be uniform in consistency and react to undue pressure differently than similar sized samples, due to the specific characteristics of the unique body tissue sample. Accordingly, available systems and methods for device testing or manufacturing are not configured to handle soft body objects, or their inherent inconsistencies. Likewise, real-time controlled systems and methods for medical procedures are not configured to handle soft body objects in an automated manner.

Accordingly, there exists a need for a robotic handling of soft tissue, potentially nonuniform or nonhomogeneous, in a dynamic and/or automated system and method. Further, there exists a need for a robotic handling of human or animal body tissue in a dynamic and/or automated system and method.

SUMMARY

Embodiments of the present invention provide a robotic control system, method and apparatus that utilizes a fused sensing stream to predict the deformation of a robotic end effector and the tissue that it is in contact with using a Finite Element Analysis model. The model updates provide adjustment parameters for the control system to compensate for changes in the mechanical nature of the robotic end effector and the tissue it is manipulating.

Embodiments of the present invention provide a robotic control system, method and apparatus that resolves the pose and force necessary to achieve an alignment of structures in the robotic end effector and the tissue being manipulated such that the aligned tissue will exert a specific force and pressure on an even deeper tissue location.

Embodiments of the present invention provide a robotic control system, method and apparatus that resolves the pose and force necessary to keep the end effector on a specific location of a tissue structure while moving along that structure such that the end effector will maintain constant contact.

Embodiments of the present invention provide a robotic control system, method, and apparatus that resolves the pose and force necessary to induce a mechanical shearing on a layer of tissue.

DETAILED DESCRIPTION

Figure 1:
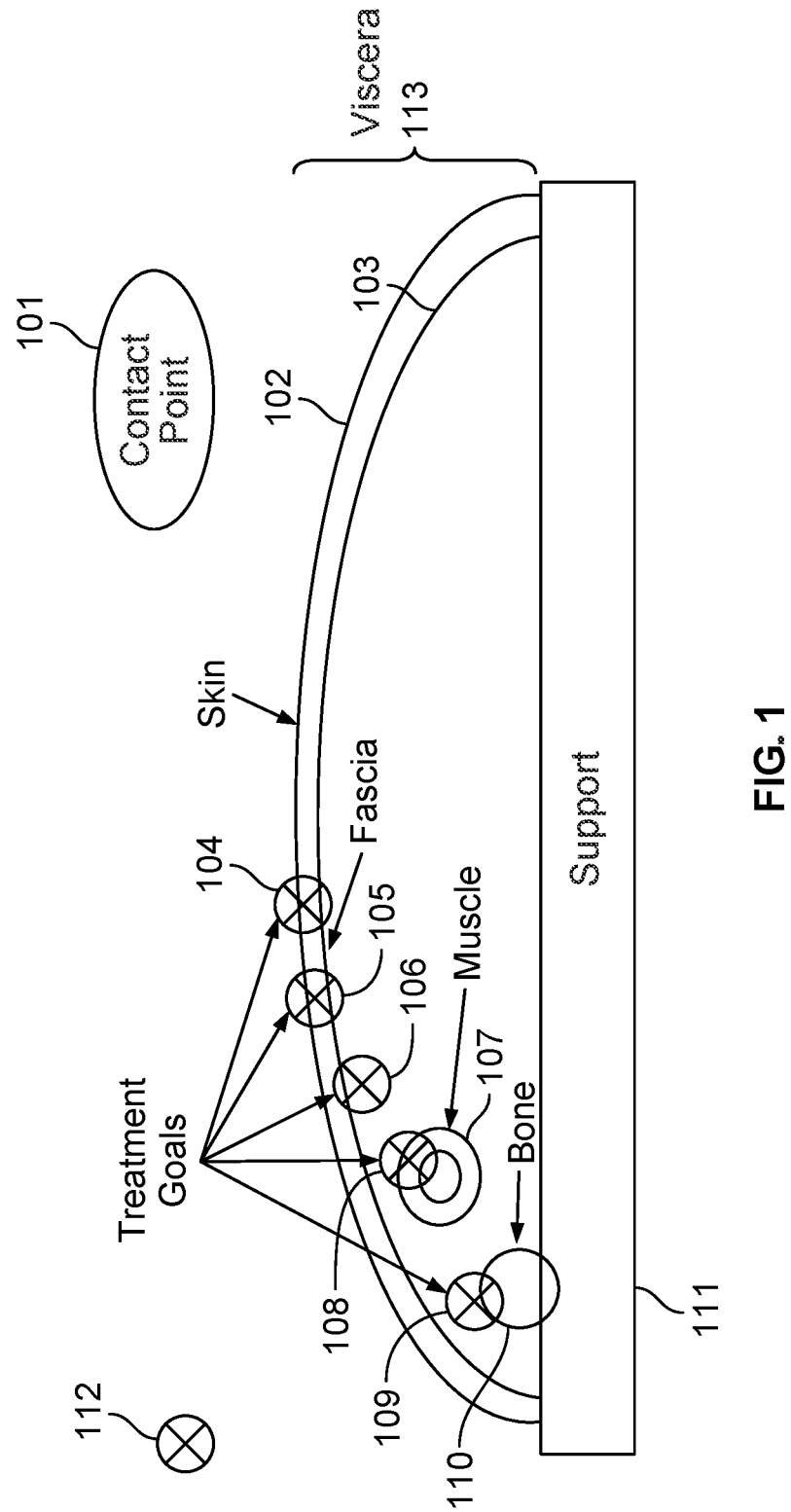
FIG. 1 shows a tissue treatment system according to an embodiment of the present invention.

The various embodiments described and illustrated are for the purpose of showing some example embodiments of the present invention and are not intended to limit in any way the scope of the present invention.

Embodiments of the present invention provide for a tissue treatment system and method. Embodiments of the present invention provide for a tissue treatment system and method for a robot applying patterns of pressure on the surface of a body in order to assess and treat in vivo tissue. Embodiments of the present invention provide for a tissue treatment system, method, and apparatus, which localizes the position of the body on the working surface or structure, detects the configuration of the body, identifies the surface regions of the body, predicts the underlying anatomy of the body, assesses the state of the body, plans manipulation of the body, and executes the plan on the body. The tissue treatment system plans treatment goals that target specific tissue, assessing the state of the tissue, and planning manipulation of the tissue that will change the tissue state.

Contact with an object or soft body has certain complexities; contact with a human body and/or specific body tissue involves additional complexities. Accordingly, embodiments of the present invention involve additional sophistication measures to the robotic sensing, planning, and control loop. In embodiments, the layers of control are a composite of planning at the object, body, and tissue level that are all combined into a single plan and set of goals that are executed and adapted in order to achieve the intended tolerances. The intended tolerances can be preset thresholds or values. The intended tolerances can be dynamically set thresholds or values. The intended tolerances can be that of a human using the robot to originally record a manipulation and using the values from that recording to be the intended tolerances.

In embodiments, the motion plan is a treatment being applied by a robotic system to a bodily structure comprising soft and/or hard tissue. The treatment goals can include one or more of: light stimulation of skin, moderate pressure contact to somewhat displace the skin from the subcutaneous fascia, higher pressure contact to displace, compress, and mobilize muscle tissue, and higher pressure contact to mobilize skeletal structures.

In embodiments, the motion plan is modified during execution as the tissue treatment system detects and localizes adhesions within the tissue. In embodiments, the motion plan is modified when the system detects and localizes areas of higher than baseline tissue stiffness. In embodiments, the modifications include the addition of motions specifically designed to target the treatment of these problem areas. The modifications are inserted into the middle of the motion plan, as appropriate, to achieve smoothness and continuity of motion. In embodiments, in addition to automated detection, additional treatment motions can be inserted as desired by the user through an interaction with the user interface panel.

Palpation is the sensing and manipulation of tissue, determining its locality and state. In embodiments, specific states of tissue are targeted, manipulation is performed on the tissue in that state, and the state is reassessed in order to determine if further treatment is needed or whether a desired change in the tissue state is achieved.

FIG. 1 shows an example tissue treatment system and method. In an embodiment, the tissue treatment system and method has contact point 101, viscera 113, and support 111. The contact point 101 is on the surface of a touch point that is in contact with the surface or skin 102 of the subject or body undergoing treatment. Below the subject's skin, the viscera is made up of various tissues, including subcutaneous fat and connective tissue, muscle, bone, organs, and other tissue. Below the viscera is a rigid support 111 shown that acts to prevent the viscera from spatially translating when fully compressed. The system moves the contact point into contact with and along the skin 102. The planned contact of the contact point with the skin is defined by at least one of a plurality of treatment goals 112.

FIG. 1 shows the parts of the viscera 113, including 102 is the surface of the skin and the subsurface tissue from the skin to the fascia 103, 107 is muscle for which an interior region of the muscle denotes a circulatory vessel, 110 denotes bone. FIG. 1 also shows goal 109 which targets the bone, goal 108 which targets the muscle, goal 106 which targets the viscera interior to the fascia, goal 105 targets the fascia, and goal 104 targets the skin region.

In an embodiment, the contact point is any point on the tool that is in contact with the tissue. In an embodiment, the contact point is a single point of contact between the tool and the tissue.

In an embodiment, the contact point is any point on the touch point that is in contact with the tissue. In an embodiment, the contact point is a single point of contact between the touch point and the tissue.

Figure 2:
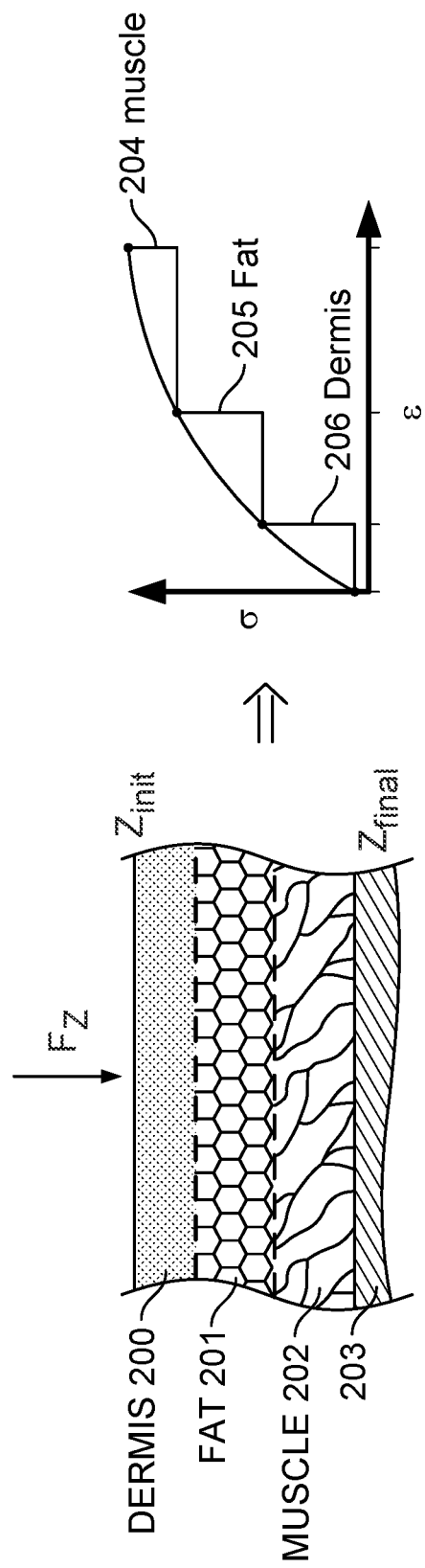
FIG. 2 shows a cross section of multiple layers of tissue according to an embodiment of the present invention.

FIG. 2 shows an example cross section of multiple layers of tissue, starting with the dermis layer 200 that is at the surface of the body, followed by the fat layer 201 below the dermis layer 200, the muscle layer 202 below the fat layer, and some other layer 203 below the muscle layer 202. FIG. 2 also shows a graph which illustrates the elastic deformation relationship between different tissue layers when arranged as on the left with a force applied from the top F.sub.z downward. For example, when there is compression of the combined structure that contains dermis stacked on fat, while the fat is stacked on muscle, as the force is increased (sigma), the deformation (epsilon) increases based on the position of the tissue in the structural stack and based on each tissue's material properties. In effect, the highest young's modulus will deform first until it cannot be further deformed, and then the next least inelastic material will begin to deform. Reference 204 illustrates when the muscle and fat are compressed completely. Reference 205 illustrates when the fat is compressed completely and the muscle is starting to be compressed. Reference 206 illustrates the compression of the dermis (which is much shallower than the other two layers) and it compresses first. In an embodiment, this is how we determine the tissue layers, as more force is applied, one sees these transitions in terms of more force being applied causing more deformation and movement into the body is increased. This provides a prediction or confirmation of the constituency and dimension of each layer, and also provides an indication as to the state of the layer, i.e., the stiffness of the layer.

Figure 3:
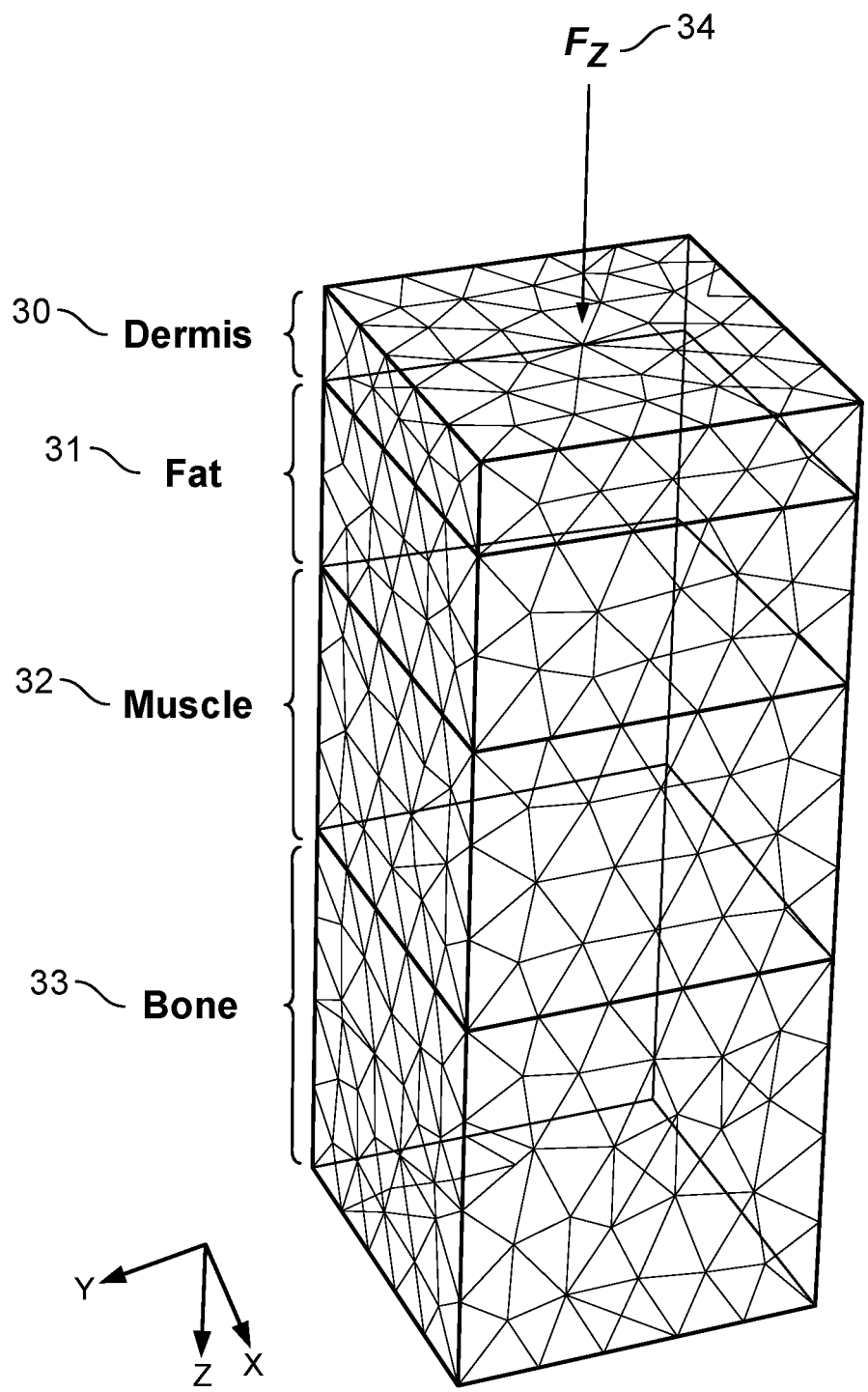
FIG. 3 shows an example finite element analysis model according to an embodiment of the present invention.

FIG. 3 shows a tissue structural model with vertices connected by edges, specifically, a Finite Element Analysis (FEA) model. In an embodiment, the components of the model are arranged to model the mechanical properties of a tissue model similar to the tissue cross-section of FIG. 2. The surface of the body is represented by the dermis layer 30. Below the dermis layer is the fat layer 31. Below the fat layer is the muscle layer 32. Below the muscle is a bone layer 33. Also depicted is the treatment pressure 34, as a force vector exhibiting a force onto the surface layer of the tissue.

In an embodiment, the tissue structural model's components are assigned material properties based on their layer assignment. For a specific treatment pressure, the tissue structural model is used in an FEA simulator to estimate the tissue deformation, tissue stiffness, and tissue strain.

In an embodiment, the tissue modeling process updates the components of the tissue structural model. The tissue modeling process utilizes modeling estimates and sensed data that is then associated with one or more components.

In an embodiment, the tissue structural model is used to infer the deformation of the surface dermis when the touch point, and more specifically the contact point, touch point, and in some cases the robot arm, obscure the visual sensors from sensing the surface deformation. In an embodiment, the position and the deformation of the touch point against the surface dermis is used to calculate the displacement of the surface using FEA of the contact between touch point and tissue structural models.

Figure 11:
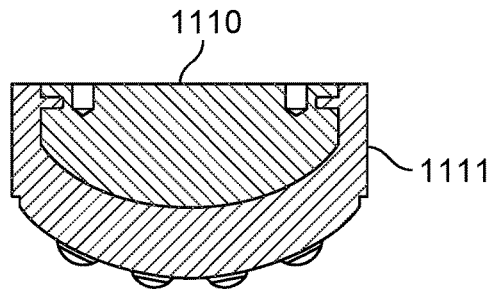
FIG. 11 shows a cross section of a touch point according to an embodiment of the present invention.

FIG. 11 depicts a cutaway or cross section view of an example touch point. The touch point is made up of a base layer 1110 and an overmolded elastomer layer 1111.

In an embodiment, the touch point is modeled as an FEA model with each layer having their own distinct material properties, referred to as the touch point model.

In an embodiment, the structure of the robot's tool, i.e., the touch point, is considered as a complex structure so that when matched to the complex structure of the underlying tissue of the body, it results in a more complex contact reference frame that needs to be managed in order to keep the robot in control and therefore able to achieve its goals within the desired or predefined or dynamically defined tolerances.

In an embodiment, the touch point model and the tissue structural model are combined into a contact model. The contact model is used to simulate the dynamic interaction of the two constituent models. The simulation estimates the contact patch between the two constituent models including the surface areas that are in contact, the friction between the surfaces, and the shear stress of the surface layers that are in contact.

In an embodiment, the constituency of the layers of the touch point are specified to match the constituency of the tissue being treated. By matching the layers, the compliance of the touch point matches the compliance of the tissue being manipulated. In an embodiment, as pressure is increased, the tissue and the touchpoint deform in a similar manner, matching their viscoelastic characteristics. In the case of pressure targeting softer tissue, the softer material in the touch point is compressing in a complementary manner. In an embodiment, when the softer tissue layer and the softer touch point layer are completely compressed and the harder layers of each are then engaged, then the stiffer interaction at higher pressure allows minor pressure variations to more efficiently manipulate the tissue. The latter hard tissue target being joint mobilization while the former soft tissue target being compression of the tissue in order to promote other state changes, including increasing blood flow, flushing lactic acid, and reducing inflammation.

In an embodiment, the treatment goals are interaction goals that have been modified to maintain alignment of anatomical structures. An embodiment provides a modification of the goals based on a sensing goal that is based on the body's thermal state, measured tissue stiffness, or detected tissue anomalies. An embodiment or further embodiment utilizes repetition of one or more treatment goals, with modification on each repetition until an event is sensed. An embodiment or a further embodiment provides a modification of the goals based on longitudinal analysis, data gathered over one or more previous sessions or entered in manually by a system operator.

In an embodiment, the alignment of the structure of the touch point and the structure of the tissue is like a stack of materials being pushed together, and, if control is not maintained, then you can have the different layers shift in undesirable ways. This embodiment combines the targeting of tissue, the alignment of the surrounding tissue, and the alignment of the touch point. It is useful to note that the compliance of the touch point combined with the touch point's contact and motion (dynamics) is able to utilize the tissue being manipulated as if it were part of the tool itself. The robot is able to manipulate in such a way that the end effector, or touch point, uses tissue to manipulate tissue.

In an embodiment, the tissue anomalies include any discontinuity in the correlation between the estimated tissue state and the actual tissue state. Those tissue anomalies with discontinuities above the treatment target threshold qualify the tissue anomaly as a candidate tissue target.

In an embodiment, the candidate tissue targets that are associated with pressure targeting the fascia interface are tagged as tissue adhesions.

Figure 4:
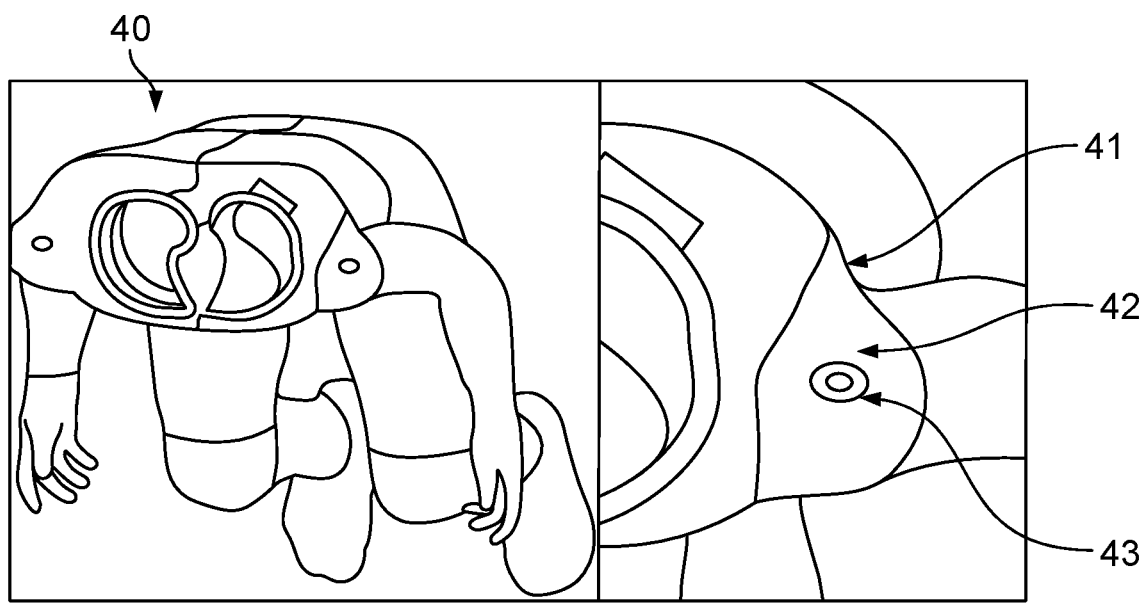
FIG. 4 shows a cutaway sample of a finite element analysis model according to an embodiment of the present invention.

FIG. 4 shows a cutaway or cross section of an FEA model 40 of a human body, the left shoulder is detailed on the right. The detailed view shows the dermis layer 41, the muscle/fat layer 42, and the bone layer 43.

In an embodiment, tissue state is assessed and the treatment goals are modified based on a desired tissue state. A treatment cycle is defined by tissue state assessment being performed, identifying treatment targets, modifying the treatment plan to apply a treatment protocol to the treatment targets at their detected location, and then reassessing the tissue state at that location to see if further treatment is required. The treatment cycle is repeated as necessary based on time constraints.

In an embodiment, the treatment cycle is chosen from predetermined treatment cycle protocols which are applicable for the desired treatment effect. In an embodiment, the treatment cycle protocols are defined by expert practitioners in the field. In an embodiment, the treatment cycle protocols are generated programmatically. The treatment cycle protocols are learned from analysis of prior treatment runs on the same or different individuals.

In an embodiment, the learned treatment cycle protocols utilize machine learning techniques, specifically deep learning, to infer protocol specifications based on treatment cycle efficacy.

In an embodiment, composite layers of tissue, and their individual states are considered when modifying the goals.

In an embodiment, treatments are a specific feedback loop enabled by the compositing of offline and online motion planning based on combining goals from object manipulation, body interaction, and tissue treatment.

Figure 5:
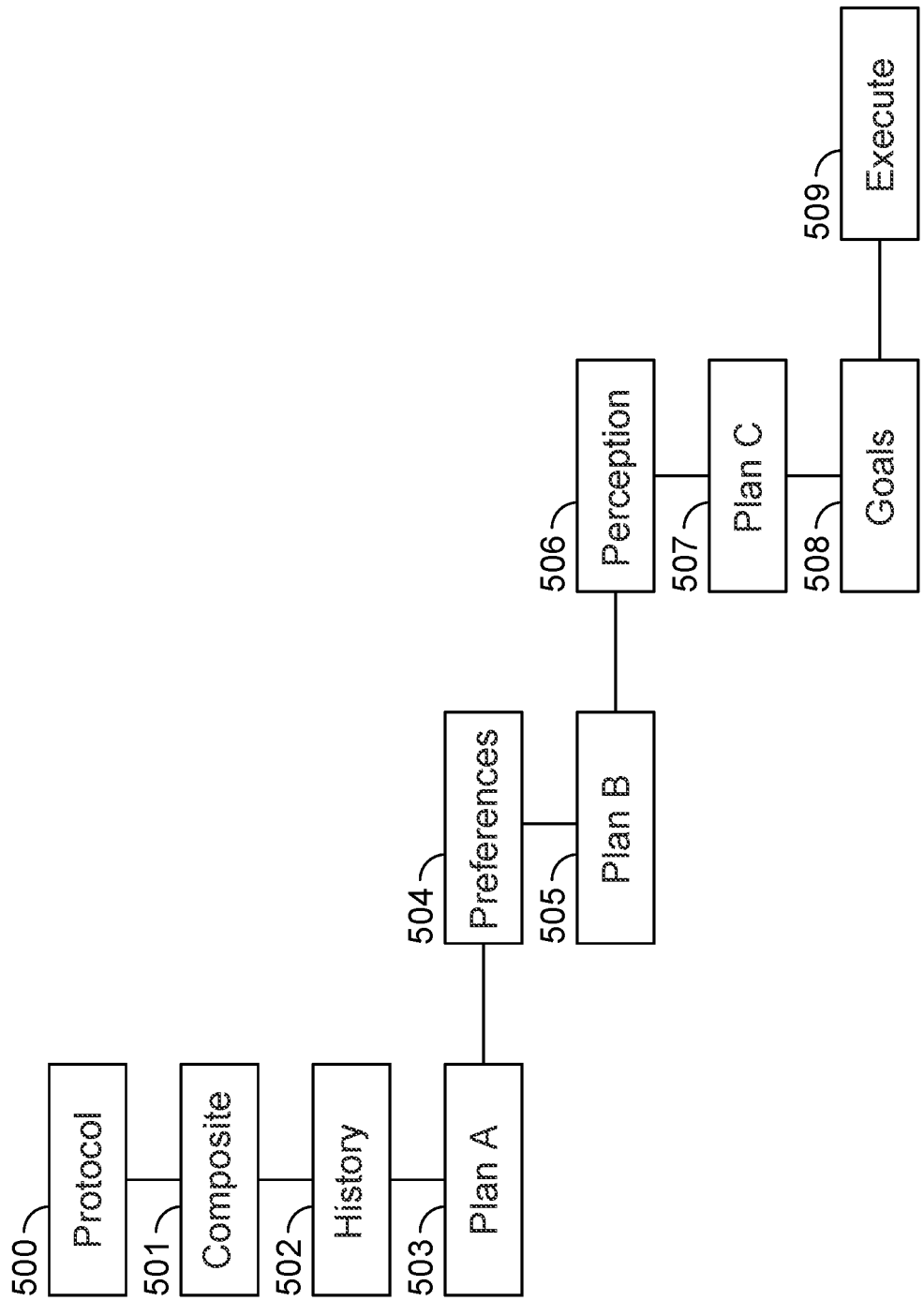
FIG. 5 shows a tissue treatment method according to an embodiment of the present invention.

FIG. 5 depicts an embodiment of the tissue treatment method/process/procedure. In the tissue treatment procedure, the protocol step 500 utilizes a set of predefined treatment protocols from which a subset of one or more protocols are selected. In the composite step 501, the selected protocols are sequenced and composited into a composite protocol. In the history step 502, historical data for the customer or client is utilized to modify the composite protocol. In the plan A step 503, the composite protocol is used to generate a plan. The preferences step 504 customizes the plan based on client preferences, resulting in a modified plan B 505. The perception step 506 includes sensed data in the further modification of the plan, resulting in plan C 507. The goals step 508 generates tissue treatment goals from the modified Plan. The tissue treatment goals are then executed in step 509.

In an embodiment, the tissue is modeled using a FEA method, resulting in a tissue model. The material characteristics are assigned to the elements representing each layer of tissue. Deformation of the surface layer of tissue is used to simulate the deformation of the underlying layers.

In an embodiment, the tissue model is registered to an anatomical model that has been morphed to match the body being manipulated. The anatomical model provides sufficient material properties to allow simulation and estimation of underlying tissue structures. The changes in the tissue structures is utilized to determine if treatment goals have been reached or whether the goals need to be modified.

In an embodiment, the tissue model is spatially registered in order to match sensed data. Sensed data includes stiffness measurements, ultrasound imaging, visible color images, depth images, infrared images, and thermographic imaging.

In an embodiment, the therapeutic planning is modified based on one or more of the following physiological marker assessments: blood flow, breathing rate, heart rate, adhesions, trigger points, client preferences, operator preferences, tissue oxygenation estimates, pulse oximetry measures. In an embodiment or a further embodiment, the modifications are made by the system in an autonomous manner, without requiring approval or oversight from a human operator. Embodiments provide for tissue sensing and modeling in addition to body modeling, as described herein, to provide a sensitive, comprehensive system and method.

In an embodiment, the physiological marker assessments include one or more of user auditory cues, user facial expressions, and live user feedback.

In an embodiment, historical data is collected for each treatment plan. The physiological marker assessments are included in the historical data.

In an embodiment, the historical data is analyzed to determine treatment plan modifications in the historical data analysis process. In an embodiment, the historical data for one or more users is included in the historical data analysis process.

In an embodiment, the treatment goals include a percussive manipulation specification. The specification indicates an additional pattern of motion and pressure that is used to sample the coupling of the touch point and the tissue to determine the constituency, state, and orientation of the tissue.

In an embodiment, the treatment goals include a shearing manipulation specification. The shearing manipulation induces a pressure to compress the tissue and a perpendicular pressure to move one layer of tissue relative to the layer below it. When this shear manipulation targets moving one layer over another layer, where the interface between the layers is the fascia, the sensed resistance and stiffness gives an indication of the state of the fascia. In a further embodiment, the state of the fascia is used to resolve unwanted connections between the tissue layers, or adhesions.

An embodiment provides for a particular form of manipulation that is challenging for a human person to achieve, but given the higher sensitivity of the robot sensing system, and, e.g., its force/pressure sensing advantages over the human senses. In an embodiment, the control system maintains a precise level of pressure that facilitates a shearing action on specific tissue layers with a fidelity that is difficult for humans to achieve.

Figure 6:
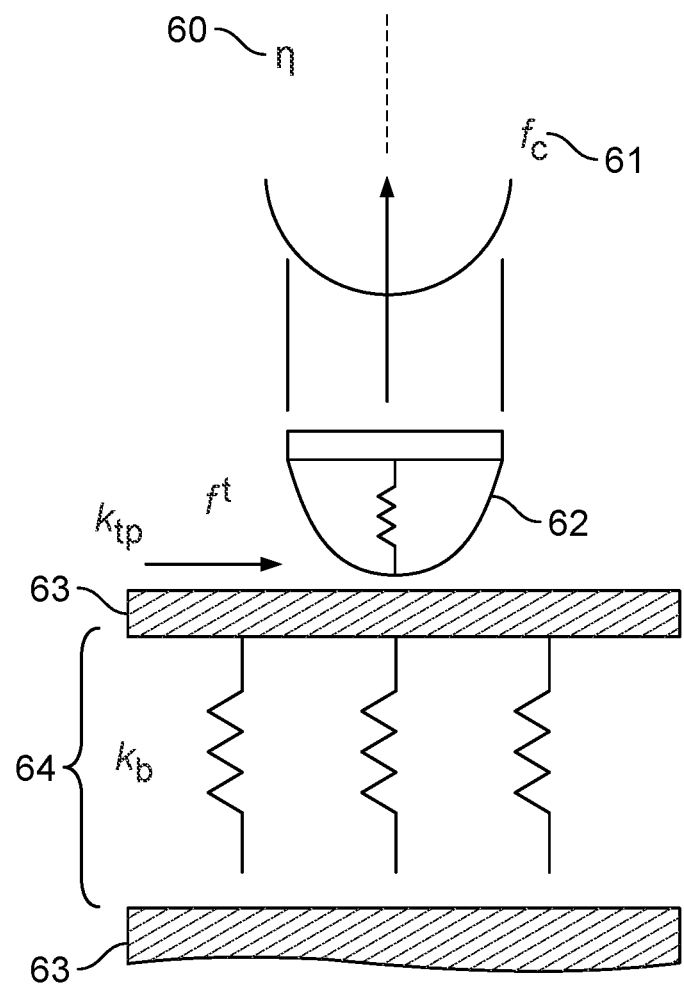
FIG. 6 shows a stiffness assessment model according to an embodiment of the present invention.

FIG. 6 shows a stiffness assessment model embodiment. In FIG. 6, the surface normal 60 is the direction perpendicular to the tangent plane of the surface 63 at the point the touch point 62 is in contact. There is a force component 61 parallel to the surface normal 60 and a complementary orthogonal component of the force that is parallel to the tangent of the surface 63 that is in contact with the touchpoint 62. There are spring constants that are used to model the elastic deformation of the touch point, $k_{tp}$, and $k_b$ 64 representing the elastic deformation spring constant of the object with which the touch point is in contact. In an embodiment, the $k_b$ 64 of the object is notionally backed by another non-deformable and immovable surface 63.

Figure 7:
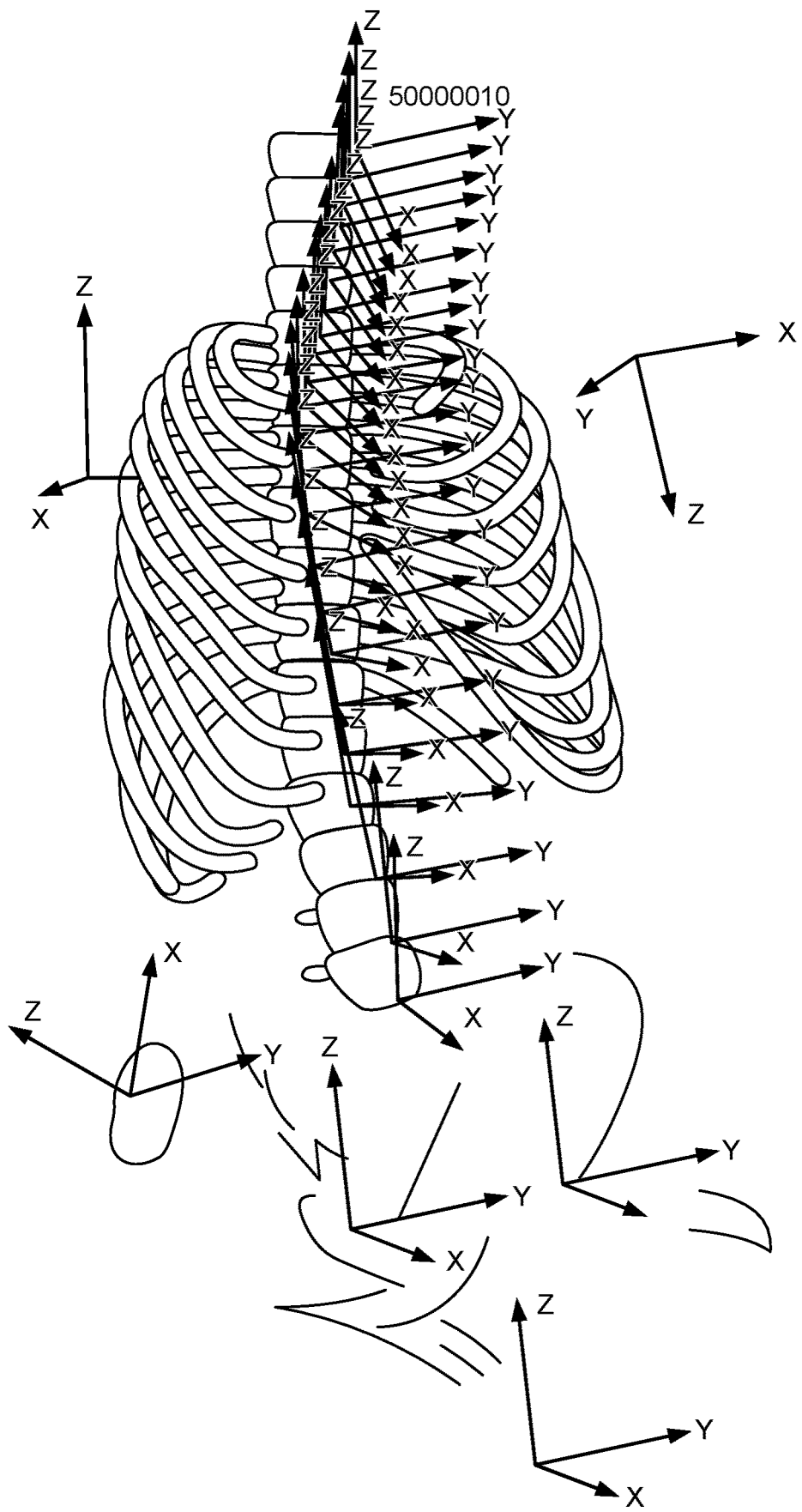
FIG. 7 shows an anatomical model according to an embodiment of the present invention.

FIG. 7 shows revealed layers of the anatomical model that is spatially morphed and registered to the subject.

Figure 8:
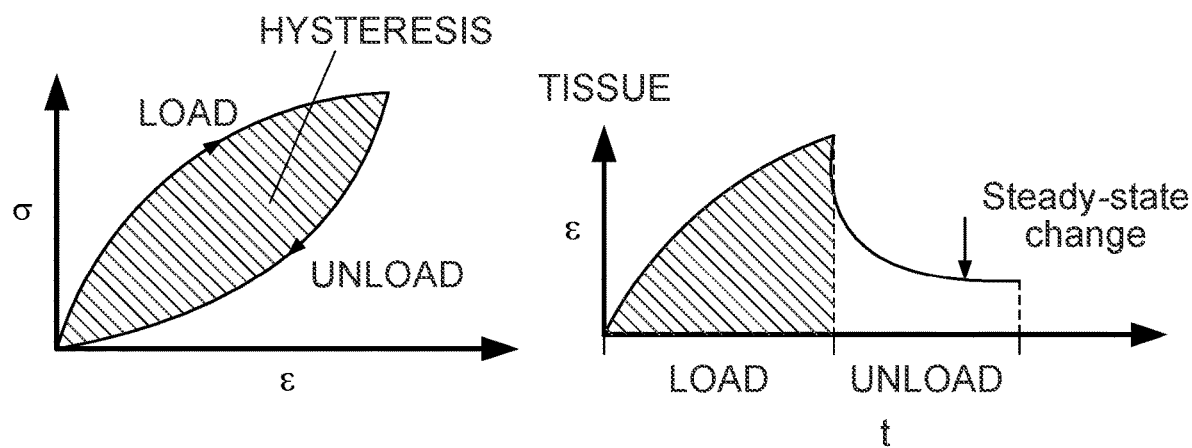
FIG. 8 shows tissue state viscoelastic properties model according to an embodiment of the present invention.
Figure 9:
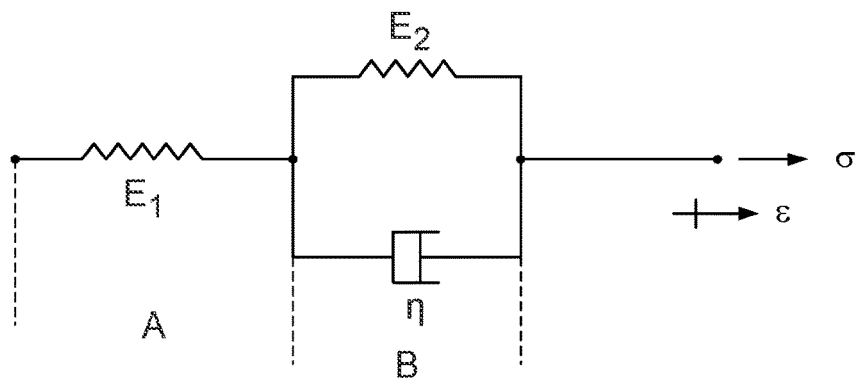
FIG. 9 shows a spring damper model according to an embodiment of the present invention.

FIG. 8 shows the tissue state viscoelastic characteristics undergoing loading and unloading of the touch point. FIG. 9 shows the spring-damper model for touch point interaction with the tissue surface.

Figure 10:
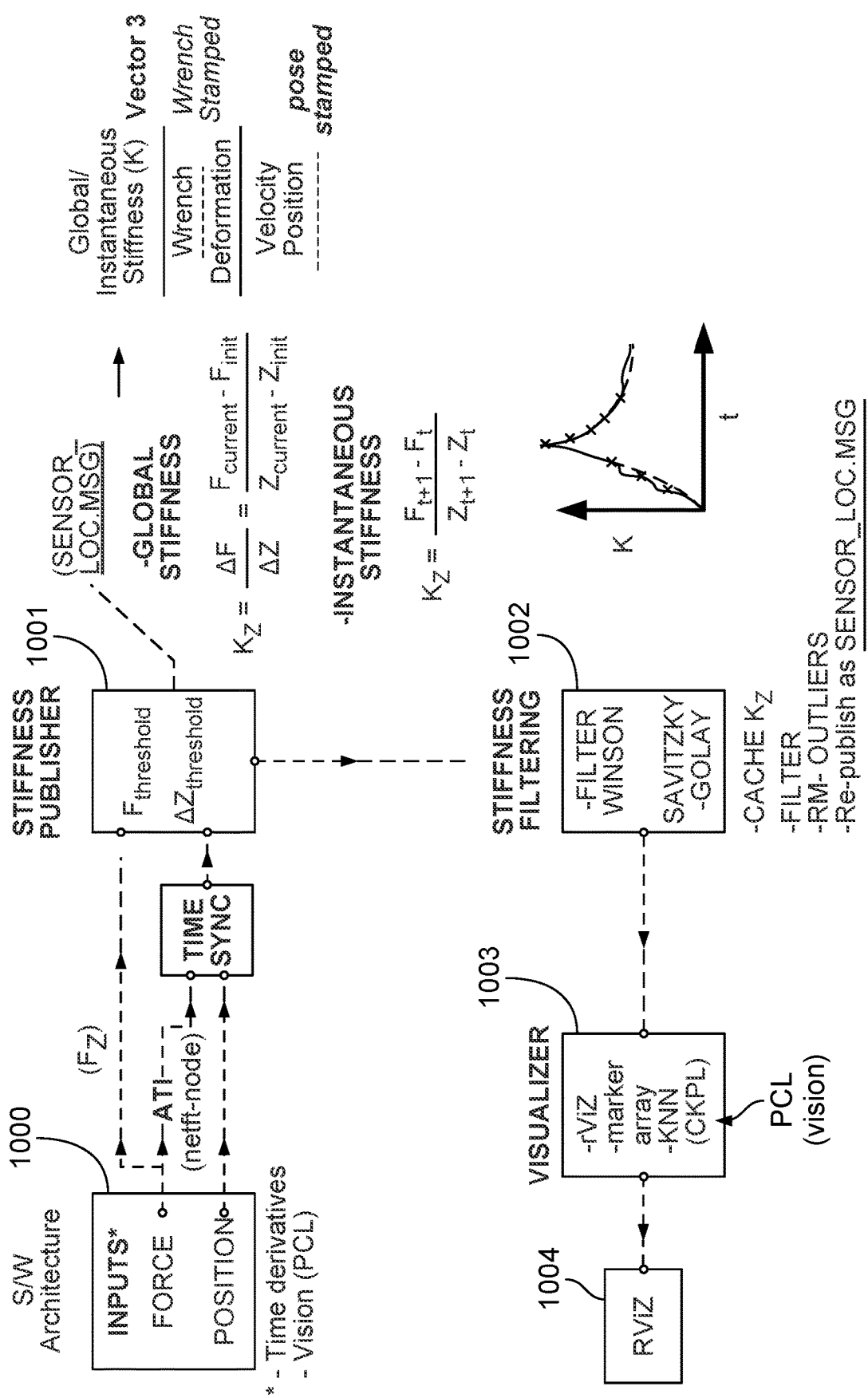
FIG. 10 shows a tissue state assessment according to an embodiment of the present invention.

FIG. 10 shows a tissue state assessment process. In an embodiment, the tissue state is assessed by combining the position displacement samples with the corresponding force measurement samples. The combination of these measurements into a bulk stiffness model yields an estimate of the bulk stiffness of the tissue. The term "bulk" is meant to be nonlimiting, referring to variation in the fidelity of the model being estimated.

In an embodiment, the bulk stiffness model combines one or more of each corresponding position displacement and force measurement, performing a bulk stiffness operation dividing the force by the displacement to calculate stiffness. In an embodiment, the bulk stiffness operation is averaging the force and dividing it by the average of the displacement.

In an embodiment, the bulk stiffness model retains the force measurement and position displacement for each specific spatial region of tissue in the tissue model. The retained values are combined into a temporal bulk stiffness model. The temporal bulk stiffness model combines the retained force and stiffness samples using a temporal bulk stiffness operation.

In an embodiment, the temporal bulk stiffness operation performs a time-averaged operation on the position displacement and force measurement samples individually before dividing the average force by the average displacement. One or more of these products is combined using a bulk stiffness operator.

Embodiments of the present invention provide for an estimation modeling technique based on a sparse sampling followed by interpolation of the values two areas that were not directly measured.

In an embodiment, the position displacement is generated relative to the contact reference frame. The position displacement is calculated as the difference between the contact point, the origin of the contact reference frame, and the original surface point, defined as the point on the surface of the body that intersects a line co-linear with the z-axis of the contact reference frame. In a further embodiment, the z-axis of the contact reference frame is collinear with the force measurement force vector. The original surface is the surface position of the body prior to being deformed by the touch point. In a further embodiment, the force measurement is the measured external force rather than the difference of measured external forces.

In an embodiment, the position displacement is determined by calculating the difference between the contact point and the original surface point that intersects a line collinear with the force measurement force vector. The original surface is the surface positions of the body prior to being deformed by the touch point. In a further embodiment, the force measurement is the measured external force rather than the difference of measured external forces. The contact frame stiffness is estimated from this force measurement divided by the position displacement.

In an embodiment, the position displacement and force measurement samples are measured differentially relative to the previously recorded corresponding sample of each, termed a differential stiffness sample. These differenced values are utilized in lieu of the original position displacement and force measurement values defined in all of the bulk stiffness model and temporal bulk stiffness model embodiments.

In an embodiment, multiple differential stiffness samples are combined to generate a spatial representation of all samples into a differential stiffness map.

In an embodiment, a homogeneous material modeling process samples one or more differential stiffness samples from the differential stiffness map, and generates a homogeneous material model. In a further embodiment, the homogeneous material modeling process averages the force measurement samples and divides this product by the average of the position displacement samples. In a further embodiment, a selection of the samples is based on their proximity to a region of interest for which a stiffness approximation is required.

In an embodiment, the homogeneous material fitting process utilizes the data in the homogeneous material model to calculate parameters for an analytical model of the material. These analytical models include auto-regressive models, models that estimate the Young's modulus.

In an embodiment, the homogeneous material fitting process utilizes a high parameter approximation of the material model. Common machine learning techniques can be used to approximate the model.

In an embodiment, the material model is represented spatially using an FEA Model. In an embodiment, the material model is represented spatially using a particle model.

In an embodiment, the embodiments describing the differential stiffness model can apply to the stiffness model.

In an embodiment, the embodiment(s) describing the differential stiffness model apply to the contact frame stiffness.

In an embodiment, a material segmentation process segments the different materials in the model. The material segmentation process segments by analyzing the characteristics of the model, including stiffness magnitude, displacement direction and spatial placement. The differential stiffness map is used to segment the materials based on defining a feature space from one or more of the following: stiffness magnitude, displacement direction, and spatial placement. The feature space is then segmented, yielding a segmentation of the material.

In an embodiment, where a sampled object contains multiple materials or material states the differential stiffness map can be used to segment the materials by fitting an existing FEA model to the data. In a further embodiment, a probability is assigned to estimate the material type.

In an embodiment, the differential stiffness bulk model and stiffness bulk model include higher order kinematics of the contact model, augmenting the sampled data with velocity, acceleration, directional components of the position and force measurements. The augmented data is utilized to extend the modes to better resolve the material properties for spatial groupings of bulk stiffness estimates.

In an embodiment, the force delta is the change of disturbance force. The disturbance force is the difference between the commanded force and the measured force. In a further embodiment, the force delta used to calculate the differential stiffness bulk model. In a further embodiment, the force delta values are integrated based on the velocity at the time of measurement.

In an embodiment, the stiffness modelling process includes all combinations of the operations that generate the differential stiffness bulk model and stiffness bulk model.

In an embodiment, the stiffness modelling process utilizes the torque sensors in the robot arm to derive the measurement of the external force wrench.

In an embodiment, the stiffness modelling process utilizes a force/torque sensor mounted inboard of the end effector on the robot arm to derive the measurement of the external force wrench.

In an embodiment, the stiffness modelling process utilizes a force/torque sensor incorporated into the touch point end effector on the robot arm to derive the measurement of the external force wrench.

In an embodiment, force sensing sensors are utilized to determine the external force being exerted on the touch point by an external disturbance, specifically the body with which the touch point is in contact, and more specifically the tissue on the surface of the body with which the touch point is in contact. Force sensing sensors include, but are not limited to, pressure sensors, six axis force/torque sensors, single axis load cells, arrays of single axis load cells, and joint torque sensors.

In an embodiment, the stiffness modelling process utilizes two or more force sensing sensors incorporated into the touch point end effector on the robot arm to derive the measurement of the external force wrench. A further embodiment utilizes any combination of force sensing devices to resolve the force wrench.

In an embodiment, the contact patch on the touch point is the area that the touch point contacts the surface. Force and torque measurements are extrapolated to the contact patch, yielding contact patch force and torque estimates for the components of the model corresponding to the contact patch and subsequent deformations of the touch point and surface/tissue models, these extrapolated force estimates, along with their corresponding spatial displacements, are collectively referred to as the extrapolated contact parameters. This is useful to the system and method. It extends the force sensing of the robot to pressure sensing along a specific patch of the surface area of the robot's tool, touchpoint, against the body. In an embodiment, calculating this contact patch provides a frame of reference for controlling the robot.

In an embodiment, the force filtering process utilizes the force measurements at the end effector of the robot are low pass filtered to isolate the force component associated with tissue material constituency and tissue state. In a further embodiment, the low-pass filter is implemented as a Fourier transform. In a further embodiment, the force measurement is the difference between commanded force and measured force. In a further embodiment, the signal is resampled with respect to a uniform distance interval between samples.

In an embodiment, the contact patch generation process utilizes the low-pass filter in the force filtering process to remove the low frequency force signal. The residual higher frequency force data is then analyzed to estimate the contact patch. In an embodiment, the model of the touch point is utilized to project the higher frequency force data to the surface of the touch point incident with the direction of the force vector. The higher frequency force data content is distributed at the projected surface point using a patch assignment operator. In an embodiment, the patch assignment operator is implemented as a 2D Gaussian distribution with a standard deviation parameter based on the magnitude of the higher frequency force data.

In an embodiment, the higher frequency force data is utilized to resolve tissue structures. Rough and homogeneous tissues are represented by higher and small frequency samples, respectively.

In an embodiment, static interaction is modelled relative to tissue and morphological variations. The targets on the body are interacted with in a static mode in order to establish baseline measurements of different body tissue. This interaction is termed "exploratory indentation."

In an embodiment, dynamic interaction is modelled using regular samples that are recorded while the touch point is undergoing high order dynamics.

In an embodiment, a Hertzian elastic contact model is used to model the point contact, surface friction, normal forces, and interface adhesion.

In an embodiment, the treatment plan has a sampling phase which defines manipulation goals for assessment of tissue state. Tissue state is analyzed from one subject to another and for one subject over multiple sampling phases over time.

In an embodiment, thermal imaging is utilized to filter the tissue state samples.

In an embodiment, the Mobilization is similar to body mobilization performed by massage and physical therapists.

In an embodiment, the body features being identified include boy sport and areas of inflammation.

In an embodiment, the body features being detected and identified include rigid inclusions. These rigid inclusions include hard tissue such as bones.

In an embodiment, the stiffness modelling process utilizes one or more ultrasonic haptic sensors incorporated into the touch point end effector on the robot arm to generate and recover a tissue density estimate.

In an embodiment, the stiffness modelling process utilizes one or more ultrasound transducers incorporated into the touch point end effector on the robot arm to generate and recover a tissue density estimate.

In an embodiment, the differential stiffness analysis includes the analysis resulting in the identification of adhesions, identifying tissue state change, and identification of variations of the tissue from a canonical model over time.

In an embodiment, a user will specify preference(s) before any tissue treatment begins. These preference(s) can be information on areas to avoid completely and areas in need of extra attention. The latter preference of areas in need of extra attention is an indication of areas which are likely to have an issue to be addressed with tissue treatment. In an embodiment, during the tissue treatment process, the user can use the same interface tablet to provide useful feedback to the system in the form of responses. Responses can indicate areas where there is a high level of discomfort or a level of force at which there is discomfort.

In an embodiment, the touch point includes a Myoton mechanism to provide repeatable estimates of tissue quality. The Myoton mechanism performs punctual measures of biomechanical and viscoelastic properties to the touch point In an embodiment, the touch point is a LVDTs (Linear Variable Differential Transformer) with a built-in Hall-Effect sensor that is used to measure the external force.

In an embodiment, the touch point utilizes a pneumatic device, e.g., air floats with variable stiffness.

In an embodiment, the touch point includes an array of ultrasound transducers to provide information about the tissue layers. A further embodiment combines the array of ultrasound signals generated by the ultrasound transducers and the percussive motion to generate an elasticity map of the tissue based on ultrasound elastography.

In an embodiment, robot teleoperation using a haptic mechanism obtains force feed back from a ultrasonic-based elastic information. This allows for the addition of a human in the loop to evaluate the feeling of the tissue elasticity while teleoperating the robotic system.

Figure 12:
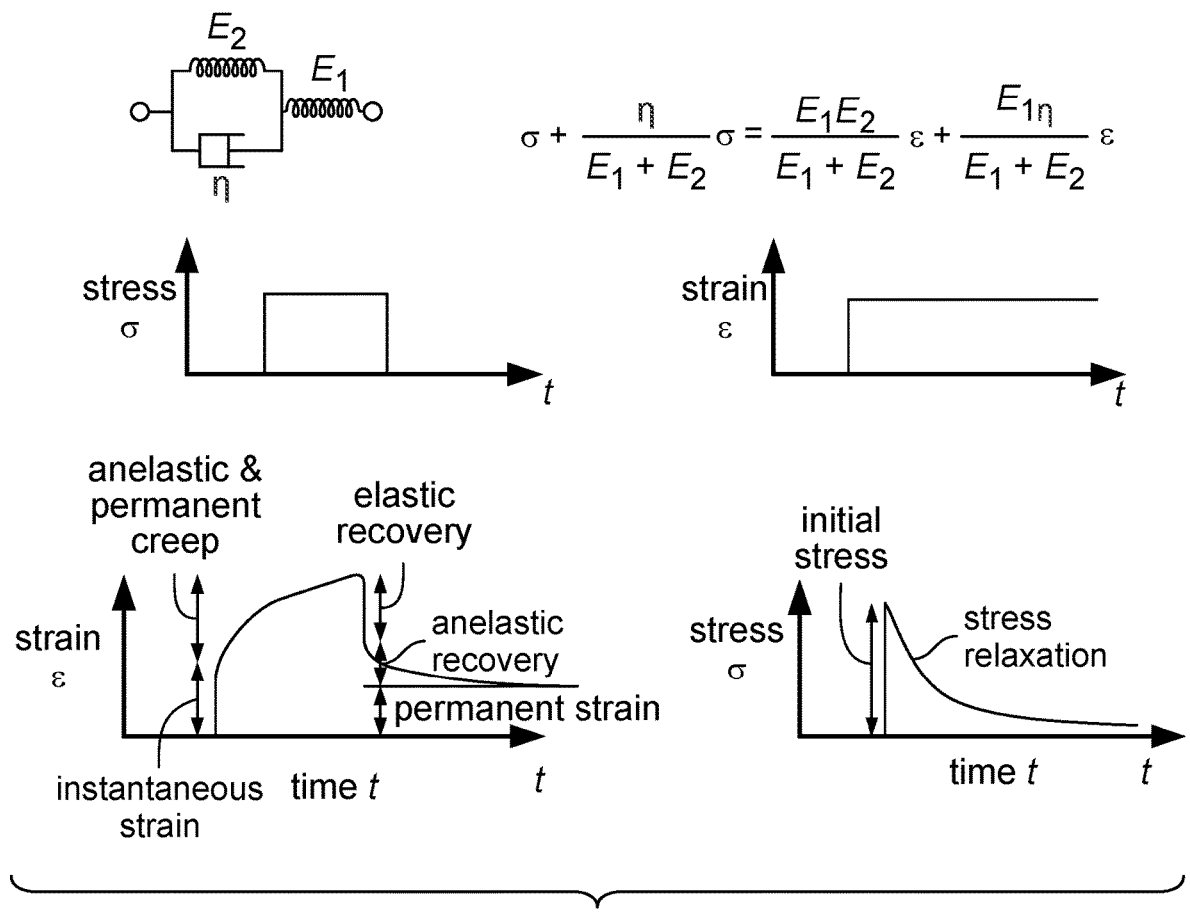
FIG. 12 shows example force modulation strategies according to an embodiment of the present invention.

FIG. 12 shows force modulation strategies which are utilized to identify and characterize tissue anomalies. In an embodiment, lateral forces are modulated with a sinusoidal pattern with a mean frequency as a force modulation strategy. In an embodiment, normal forces are modulated with a second order reactive autoregressive model as a force modulation strategy.

Figure 13:
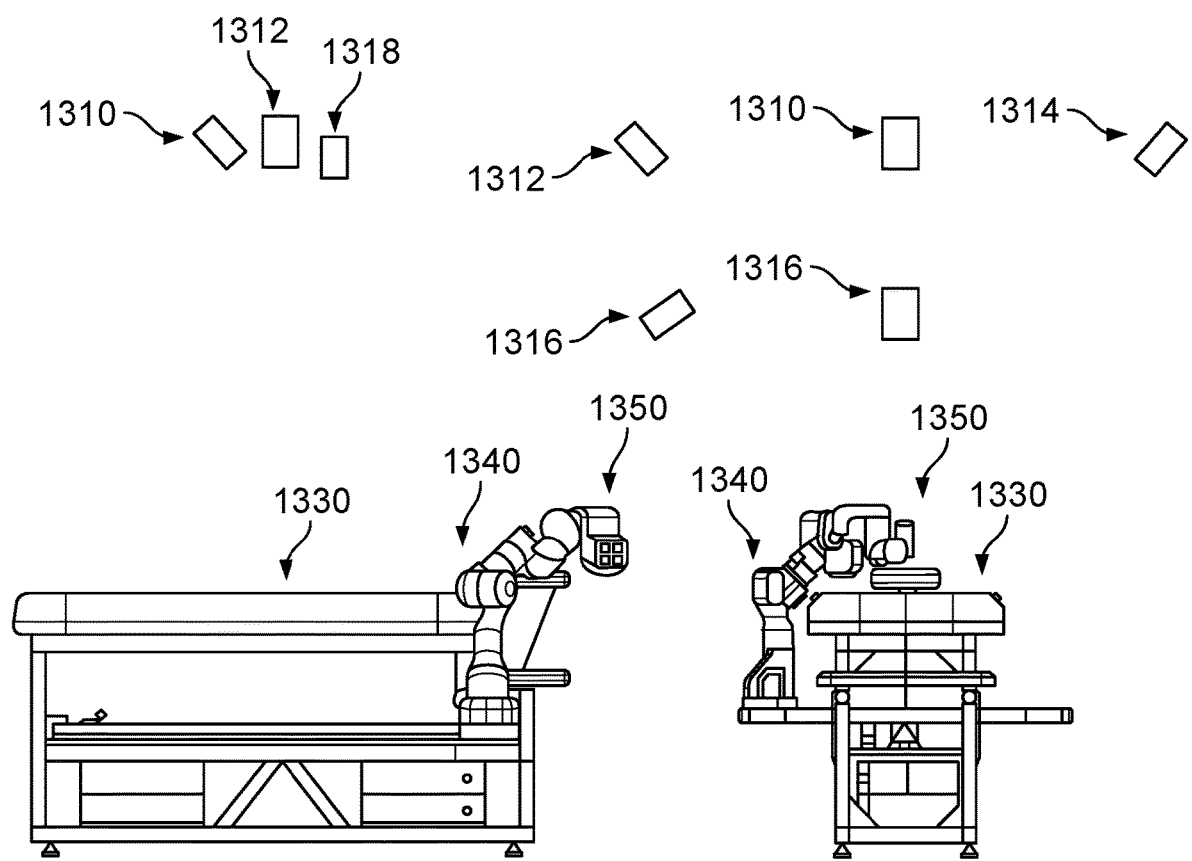
FIG. 13 shows an example system according to an embodiment of the present invention.

FIG. 13 shows a robotic system's vision components situated above and in front of the robot. These components are how the system senses an object to be manipulated, providing the data that is resolved into one or more models of the body and to characterize the tissue of the body. Several sensors 1310, 1312, 1318, 1314 are arranged above the table 1330 arranged such that when their data is combined there is a more complete and more validated view of the body and provides a characterization of the tissue. These sensors can be configured to generate thermographic imagery, visible light imagery, infrared imagery, and 3D range sensing. The robot arm 1340 is shown attached to the table, and the robot manipulator's end effector tool 1350 is at one end of the arm, and at the other end, the robot is attached to the table 1330.

Figure 14:
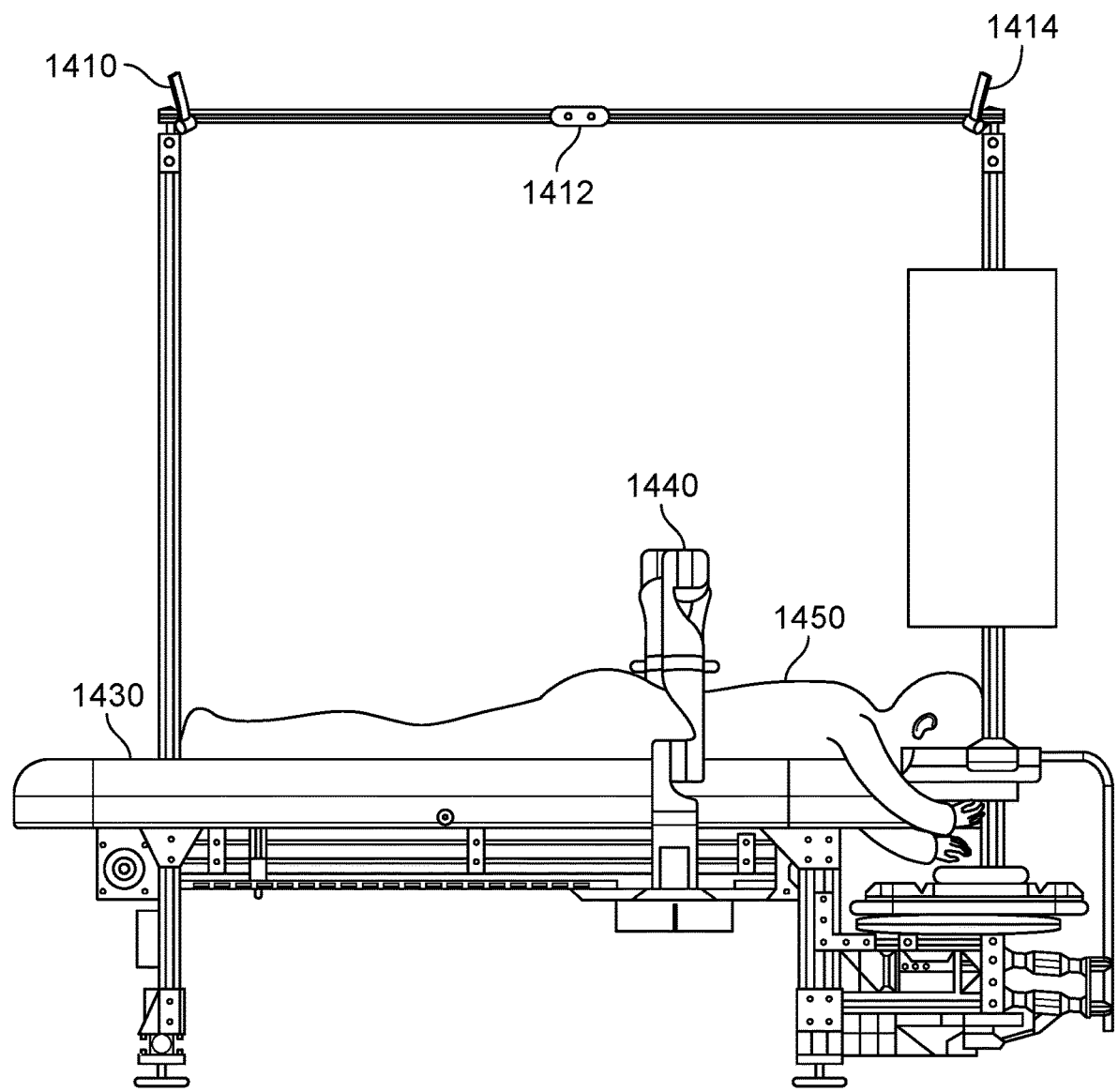
FIG. 14 shows an example system according to an embodiment of the present invention.

FIG. 14 shows the robotic system with a body 1450 and its constituent tissue as the object being targeted for manipulation. The robot arm 1440 is shown in contact with the tissue on the surface of the body 1450, and the other end of the arm is shown attached to the table 1430. Also depicted are sensors 1410, 1412, 1414 mounted above the table 1430 such that the sensor's frustums provide a redundant and comprehensive view of the body 1450 on the table 1430.

In an embodiment, natural palpation patterns are sampled from human therapist demonstrations. The natural palpation patterns are further refined based on the pattern reaction to external measured force patterns. These natural palpation patterns are refined into natural palpation protocols which determine thresholds and geometric pattern repetitions that detect, isolate, and alleviate anomalous inclusions in tissue.

In an embodiment, the artificial tactile exploration includes a set of behavioral guidelines that maximize the efficiency of probing devices by utilizing force-velocity modulation strategies.

In an embodiment, the palpation process includes local examination and global examination. The global examination includes broad strokes along the intended trajectory, commonly known as effleurage. In an embodiment, the global examination includes one or more of general body scanning and tissue state assessment. The local examination includes, focused pressure within a selected section, for shape and depth information. In an embodiment, the local examination includes one or more of: application of intentional pressure, including light and deep pressure in order to evaluate the stiffness, size, contours and shape of the formation or of the organ. The global and local examinations are achieved through using the touch point to provide pressure application similar to the pressure application of a human therapist. In an embodiment, the global and local examinations are followed by a feature discrimination process that utilizes focused pressure and the resulting sensed feedback to characterize the tissue state.

In an embodiment, the palpation process generates a sinusoidal pattern of applied force to the tissue in order to excite the tissue to a resonance frequency that can be sensed. Some challenges include: pattern for visco-elastic excitation, model to represent force modulation, probe similar to human finger that can actuate and sense in the same manner as the human finger, friction anomalies, ambiguity in depth, probe motion limitation.

Embodiments of the present invention are specific to massage, physical therapy, and similar, but are not limited to such applications in industry. Embodiments of the present invention can be used for one or more of tissue manipulation treatment, e.g., light touch or stripping or x-fiber, and tissue state assessment treatment, e.g., palpation, ultrasound, and thermal properties.

Embodiments of the present invention provide for the use of multiple sensors and/or multiple types of sensors, including for use in palpation method embodiments described herein.

Embodiments of the present invention provide for a processing of the perception of the tactile signal from different sizes and depths when coupled. For example, a small nodule embedded close to the surface produces the same signal as a large nodule embedded deep in the medium. Embodiments of the present invention provide for a method and system for handling the normal and lateral loads independently at a given location, e.g., the combined lateral force forms an ellipsoid because of the morphological constraints of a human finger. Embodiments handle the motion being limited for one direction because of the distal joint of the finger.

Embodiments of the present invention provide for handling two main patterns used by subjects—sinusoidal and ramp-like modulation of the force—with relatively short convergence time.

Embodiments of the present invention provide for handling local palpation behavioral situations to improve the perception of non-homogeneous distribution in soft tissue.

Embodiments of the present invention provide for a utilization of stiffness/elastic modulus (E) estimated using the following expression:

$$E = 3f\frac{(1+v)}{8}d\sqrt{rd} - \qquad \text{a.}$$

where f is the applied force, \nu is the Poisson's ratio, r is the radius of the EEF, and d_in the indentation depth.

Embodiments of the present invention provide for operational strategy. For example, the system and method obtains force readings from a tactile probe or touch point on a body, the intended or desired palpation force is predicted according to an output of an AR model, and then the intended or desired force is translated into normal displacement of the probe or touch point.

Embodiments of the robot control include a computer or processor controlled system in which programmable actions or steps are coded via computer software program and used to tell or control the movements of the robot control. Embodiments of the method instructions can be stored on a computer-readable medium, the medium being virtual or hardware or portable or in the cloud/networked, having instructions thereon which are readable or can be made to be readable by a computer or processor so that the computer software instructions can be executed. Embodiments of the programmable instructions to control the robot or robot arm or robot arm with an end effector can be effected by a predefined set of instructions, a machine learning set of instructions in which the system receives feedback from the sensors of the robot to modify pressure, frequency of touch, and other characteristics (e.g., cold, warmth, etc.).

The modifications listed herein and other modifications can be made by those in the art without departing from the ambit of the invention. Although the invention has been described above with reference to specific embodiments, the invention is not limited to the above embodiments and the specific configurations shown in the drawings. For example, some components shown can be combined with each other as one embodiment, and/or a component can be divided into several subcomponents, and/or any other known or available component can be added. The processes are not limited to those shown in the examples. Those skilled in the art will appreciate that the invention can be implemented in other ways without departing from the substantive features of the invention. For example, features and embodiments described above can be combined with and without each other. The present embodiments are therefore to be considered in all respects as illustrative and not restrictive. Other embodiments can be utilized and derived therefrom, such that structural and logical substitutions and changes can be made without departing from the scope of this disclosure. This Specification, therefore, is not to be taken in a limiting sense, along with the full range of equivalents to which such claims are entitled.

Such embodiments of the inventive subject matter can be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose can be substituted for the specific embodiments shown. This disclosure is intended to cover any and all adaptations and/or variations of various embodiments. Combinations of the above embodiments, and other embodiments not specifically described herein, will be apparent to those of ordinary skill in the art upon reviewing the above description.

What is claimed is:

1. A method, comprising:
   receiving sensor data at a processor-implemented controller of a robotic massage system during movement of a manipulator of the robotic massage system along a surface of a deformable body, the movement of the manipulator being based on a predefined motion plan;
   determining, via the controller, a property of an anatomical layer of the deformable body based on a detected property of the deformable body;
   identifying, via the controller, at least one adjustment parameter based on the property of the anatomical layer of the deformable body;
   modifying, via the controller, the predefined motion plan based on the at least one adjustment parameter, to produce a modified motion plan, and
   determining a deformation of the surface of the deformable body based on a tissue structural model when at least one visual sensor of the robotic massage system is obscured.

2. The method of claim 1, wherein the sensor data includes data indicative of a deformation of the deformable body during the movement of the manipulator along the surface of the deformable body.

3. The method of claim 1, wherein the sensor data includes at least one of ultrasound data, color imagery, depth imagery, infrared imagery, or thermographic imagery.

4. The method of claim 1, wherein the sensor data includes data generated by at least one of: an ultrasonic sensor, a pressure sensor, a force sensor, or a torque sensor.

5. The method of claim 1, further comprising:
generating a tissue structural model for the deformable body based on the sensor data; and
modifying the modified motion plan based on the tissue structural model.

6. The method of claim 1, wherein the predefined motion plan includes a palpation protocol.

7. The method of claim 1, wherein the deformable body is a first deformable body, the method further comprising generating the predefined motion plan using machine learning and based on at least one prior massage session associated with one of the first deformable body or a second deformable body different from the first deformable body.

8. The method of claim 1, wherein the controller is configured for teleoperation.

9. The method of claim 1, wherein at least one of the predefined motion plan or the modified motion plan specifies a goal for one of: a light stimulation of a skin of the deformable body, a displacement of the skin of the deformable body, a displacement of muscle tissue of the deformable body, or a mobilization of a skeletal structure of the deformable body.

10. The method of claim 1, further comprising automatically modifying the modified motion plan, via the controller, based on at least one of a blood flow of the deformable body, a breathing rate of the deformable body, a heart rate of the deformable body, an adhesion of the deformable body, a trigger point of the deformable body, an estimated tissue oxygenation of the deformable body, or a pulse oximetry measurement of the deformable body.

11. The method of claim 1, wherein the property of the anatomical layer of the deformable body is a stiffness, and the determining the stiffness is further based on at least one of a position displacement or a force measurement.

12. The method of claim 1, wherein the determining the deformation of the surface of the deformable body is performed using a finite element analysis (FEA) model.

13. The method of claim 1, further comprising estimating a condition of a tissue structure of the deformable body based on at least one of a tissue model or an anatomical model that has been morphed to match the deformable body.

14. The method of claim 13, further comprising determining whether a treatment goal has been reached based on a detected change in a tissue property of the deformable body.

15. The method of claim 1, wherein at least one of the predefined motion plan or the modified motion plan is based on at least one of an object manipulation goal, a body interaction goal, or a tissue treatment goal.

16. The method of claim 1, wherein at least one of the predefined motion plan or the modified motion plan is configured to apply a shear force to a specific tissue layer of the deformable body.

17. The method of claim 1, wherein at least one of the predefined motion plan or the modified motion plan includes a predefined force pattern over time, the force pattern including at least one of a sinusoidal pattern or a ramp-like pattern.

18. The method of claim 1, wherein at least one of the predefined motion plan or the modified motion plan includes a palpation pattern.

19. The method of claim 1, further comprising modifying the palpation pattern based on a detected anomalous inclusion in a tissue of the deformable body.

20. The method of claim 1, wherein at least one of the predefined motion plan or the modified motion plan includes an instruction associated with a patch of a surface of the manipulator of the robotic massage system.

21. The method of claim 1, wherein the manipulator of the robotic massage system is configured to determine an estimated tissue quality of the deformable body.

22. The method of claim 1, wherein the manipulator of the robotic massage system is configured to detect at least one of a biomechanical property or a viscoelastic property of the deformable body.

23. The method of claim 1, wherein the manipulator of the robotic massage system includes a linear variable differential transformer (LVDT).

24. The method of claim 23, wherein the LVDT includes a Hall-Effect sensor.

25. A method, comprising:
receiving sensor data at a processor-implemented controller of a robotic massage system during movement of a manipulator of the robotic massage system along a surface of a deformable body, the movement of the manipulator being based on a predefined motion plan;
determining, via the controller, a property of an anatomical layer of the deformable body based on a detected property of the deformable body;
identifying, via the controller, at least one adjustment parameter based on the property of the anatomical layer of the deformable body; and
modifying, via the controller, the predefined motion plan based on the at least one adjustment parameter, to produce a modified motion plan, wherein at least one of the predefined motion plan or the modified motion plan includes a predefined motion relative to a contact patch including extrapolated contact parameters.

26. A method, comprising:
receiving sensor data at a processor-implemented controller of a robotic massage system during movement of a manipulator of the robotic massage system along a surface of a deformable body, the movement of the manipulator being based on a predefined motion plan;
determining, via the controller, a property of an anatomical layer of the deformable body based on a detected property of the deformable body;
identifying, via the controller, at least one adjustment parameter based on the property of the anatomical layer of the deformable body; and
modifying, via the controller, the predefined motion plan based on the at least one adjustment parameter, to produce a modified motion plan, wherein at least one of the predefined motion plan or the modified motion plan is a plan generated based on a Hertzian elastic contact model.

* * * * *